(12) United States Patent
Barnes et al.

(10) Patent No.: US 12,134,734 B2
(45) Date of Patent: *Nov. 5, 2024

(54) CORROSION INHIBITOR WITH IMPROVED PERFORMANCE AT HIGH TEMPERATURES

(71) Applicant: Cameron International Corporation, Houston, TX (US)

(72) Inventors: Paul Barnes, Aberdeen (GB); Tore Nordvik, Stavanger (NO); Trevor Lloyd Hughes, Cambridge (GB); Lynne Patricia Crawford, Harlow (GB); Evgeny Barmatov, Cambridge (GB)

(73) Assignee: CAMERON INTERNATIONAL CORPORATION, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/364,526

(22) Filed: Aug. 3, 2023

(65) Prior Publication Data

US 2023/0374370 A1   Nov. 23, 2023

Related U.S. Application Data

(63) Continuation of application No. 17/053,857, filed as application No. PCT/US2019/031226 on May 8, 2019, now Pat. No. 11,760,918.
(Continued)

(51) Int. Cl.
*C09K 8/54* (2006.01)
*C07D 239/04* (2006.01)
(Continued)

(52) U.S. Cl.
CPC .............. *C09K 8/54* (2013.01); *C07D 239/04* (2013.01); *C23F 11/149* (2013.01); *E21B 41/02* (2013.01); *C09K 2208/32* (2013.01)

(58) Field of Classification Search
CPC ..... C07D 239/04; C09K 2208/32; C09K 8/54; C23F 11/10; C23F 11/141; C23F 11/149; E21B 41/02
See application file for complete search history.

(56) References Cited

U.S. PATENT DOCUMENTS

| 3,025,313 A | 3/1962 | Gunderson |
| 3,502,671 A | 3/1970 | Hodge |

(Continued)

FOREIGN PATENT DOCUMENTS

| CN | 1069529 C | 3/1993 |
| CN | 101605765 A | 12/2009 |

(Continued)

OTHER PUBLICATIONS

International Search Report and Written Opinion issued in International Patent application PCT/US2019/031226 on Aug. 22, 2019, 7 pages.

(Continued)

*Primary Examiner* — Alicia Bland
(74) *Attorney, Agent, or Firm* — Jeffrey D. Frantz

(57) ABSTRACT

Compositions may include a corrosion inhibitor including a heterocyclic diamine prepared from the reaction of an alkyl diamine and an aldehyde, wherein the alkyl diamine has the general formula: R4NH(CH$_2$)$_n$NHR5, where n is an integer between 3 and 6, and R4 and R5 are independently hydrogen or a C2-C30 saturated or unsaturated hydrocarbon radical. Methods may include contacting a metal surface with a corrosion inhibitor composition, wherein the corrosion inhibitor includes a heterocyclic diamine corrosion inhibitor from the reaction of an alkyl diamine and an aldehyde, wherein the alkyl diamine has the general formula: R4NH(CH$_2$)$_n$NHR5, where n is an integer between 3 and 6, and R4 and R5 are independently hydrogen or a C2-C30 saturated or unsaturated hydrocarbon radical.

19 Claims, 1 Drawing Sheet

Related U.S. Application Data

(60) Provisional application No. 62/669,188, filed on May 9, 2018.

(51) Int. Cl.
*C23F 11/14* (2006.01)
*E21B 41/02* (2006.01)

(56) References Cited

U.S. PATENT DOCUMENTS

| | | |
|---|---|---|
| 5,530,131 A | 6/1996 | Hoffmann |
| 2016/0060520 A1 | 3/2016 | Panchalingam |
| 2018/0148632 A1 | 5/2018 | Bennett |
| 2021/0238469 A1 | 8/2021 | Barnes |

FOREIGN PATENT DOCUMENTS

| | | |
|---|---|---|
| EP | 0156631 A2 | 10/1985 |
| EP | 0188353 A2 | 7/1986 |
| EP | 0405932 A2 | 1/1991 |
| WO | 2011093439 A1 | 6/2013 |
| WO | 2018001604 A1 | 1/2018 |

OTHER PUBLICATIONS

International Preliminary Report on Patentability of International Patent Application No. PCT/US2019/031226 dated Nov. 10, 2020, 5 pages.

Extended Search in European Patent Application No. 19800096.0 dated Dec. 21, 2021, 9 pages.

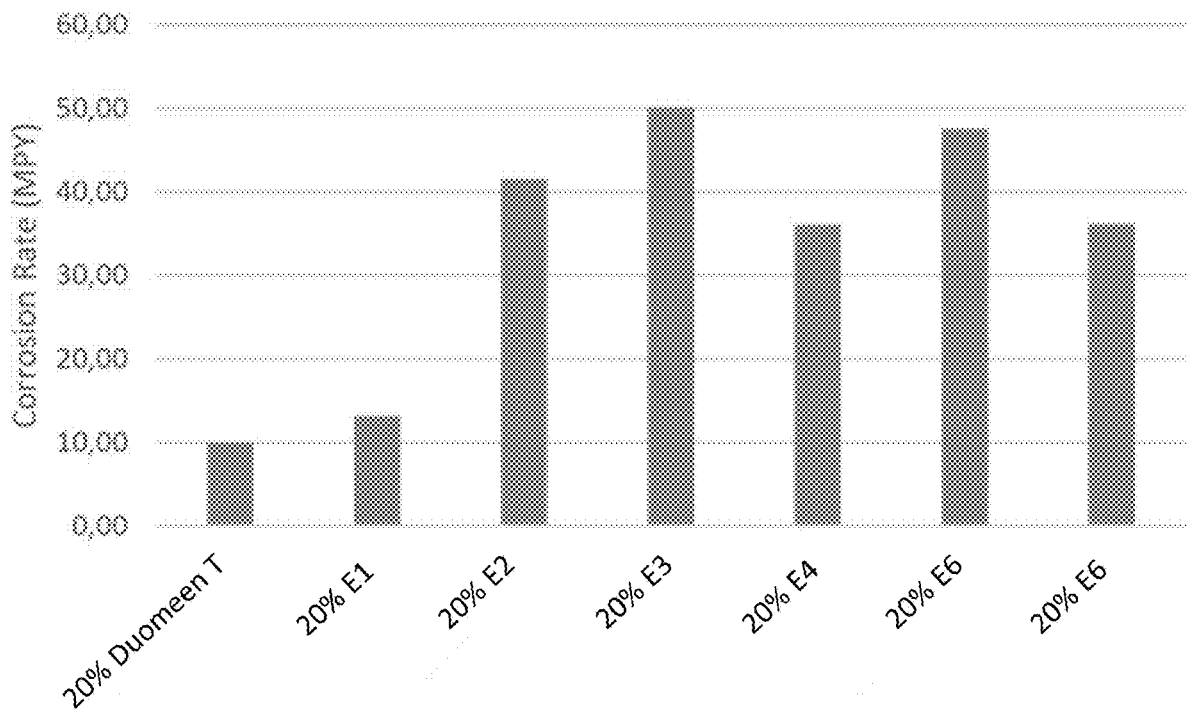

CORROSION INHIBITOR WITH IMPROVED PERFORMANCE AT HIGH TEMPERATURES

BACKGROUND

This application is a continuation of U.S. patent application Ser. No. 17/053,857, filed Nov. 9, 2020, which is a National Stage Entry of PCT/US2019/031226, filed May 8, 2019, which claims the benefit of and priority to U.S. Provisional Application No. 62/669,188, filed May 9, 2018. The above applications are each herein incorporated by reference in their entireties.

During the production of hydrocarbons from subterranean reservoirs, the downhole environment presents harsh operating conditions for downhole equipment, including high temperatures, caustic chemicals, and constrained spacing. The downhole conditions can cause impediments such as equipment corrosion and scaling that can damage downhole tools and impact tool function. Downhole scale also may lead to a reduction in productivity or performance due to obstructed flow passages.

During wellbore operations, a number of chemical and mechanical methods may be used to inhibit formation of corrosion and scale that may otherwise impact production efficiency and equipment function. One approach to inhibiting corrosion involves the metered injection of corrosion inhibiting chemicals through chemical injection lines extending from the surface. However, dosage schedules are difficult to calculate and the excessive use of corrosion inhibitors can introduce significant material costs and oversaturation of inhibitors in the produced fluids. Matters are complicated further by the fact that many scale inhibitors may degrade or become ineffective even at high concentrations, allowing for the continued growth of scale and the risk of tool damage from corrosion and locking up.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to compositions that may include a corrosion inhibitor including a heterocyclic diamine prepared from the reaction of an alkyl diamine and an aldehyde, wherein the alkyl diamine has the general formula: R4NH(CH$_2$)$_n$NHR5, where n is an integer between 3 and 6, and R4 and R5 are independently hydrogen or a C2-C30 saturated or unsaturated hydrocarbon radical.

In another aspect, embodiments disclosed herein relate to methods that may include contacting a metal surface with a corrosion inhibitor composition, wherein the corrosion inhibitor includes a heterocyclic diamine corrosion inhibitor from the reaction of an alkyl diamine and an aldehyde, wherein the alkyl diamine has the general formula: R4NH(CH$_2$)$_n$NHR5, where n is an integer between 3 and 6, and R4 and R5 are independently hydrogen or a C2-C30 saturated or unsaturated hydrocarbon radical.

Other aspects and advantages of the claimed subject matter will be apparent from the following description and the appended claims.

BRIEF DESCRIPTION OF DRAWINGS

FIG. 1 is a graphical representation of corrosion rate for a number of samples in accordance with the present disclosure.

DETAILED DESCRIPTION

In one aspect, embodiments disclosed herein relate to heterocyclic diamine corrosion inhibitors that prevent or mitigate the corrosion of metals, particularly equipment and tubing for use in wellbore operations in high temperature high pressure (HTHP) conditions. Heterocyclic diamine corrosion inhibitors in accordance with the present disclosure may exhibit surfactant and electrostatic properties that enable film formation on metal surfaces even at elevated temperatures, increasing treatment duration and minimizing the effective concentration needed to treat corrosion. Heterocyclic diamine corrosion inhibitors in accordance with the present disclosure also mitigate the corrosion of metal materials and equipment employed in wellbore operations and similar processes where corrosive fluids and/or gases are present in process streams.

Corrosion describes reaction processes that occur over relatively long time frames when metals and other materials are exposed to corrosive agents in the surrounding environment. Corrosion affects metal tool surfaces and tubing in contact with petroleum, acids, caustics, and other compounds present in injected and produced fluids, which can lead to damage and failure of downhole equipment. Similarly, equipment used to handle and transport corrosive fluids at the surface and within pipelines may be affected by corrosion. Reactive surfaces are often treated with corrosion inhibitors by coating or emplaced within process streams contacting the surfaces.

One mechanism of corrosion inhibition is the formation of a hydrophobic barrier on metals, which prevents contact of metal surfaces with aqueous fluids containing oxidative species that initiate corrosion reactions. Corrosion inhibitors may have multiple chemical functionalities, including a portion of the molecule that interacts with metal surfaces, anchoring the molecule from solution, while a hydrophobic portion or "tail" of the molecule associates with neighboring molecules to generate a hydrophobic barrier film.

However, while standard corrosion inhibitors may be used at lower temperatures with success, many exhibit poor performance at elevated temperatures, particularly at downhole temperatures and pressures. Corrosion inhibitor instability may be linked to the increase in solubility of the inhibitor in the surrounding media and various chemical degradation processes, leading to a breakdown of the protective hydrophobic film on metal surfaces and exposure to corrosive chemicals. For example, elevated temperatures may lead to an increase in hydrolysis reactions that attack the constituent bonds of inhibitor molecules, including amides, esters, ethers, and the like. Elevated temperatures may also increase the solubility of the corrosion inhibitor in solution, reducing film forming and disrupting the hydrophobic barrier. The ionic strength of the media surrounding treated surfaces is another consideration, as increasing the concentration of ions in solution may impact both the solubility of the corrosion inhibitor in the surrounding media and the affinity of the corrosion inhibitor for the metal surface.

In addition, corrosion issues may be compounded by the precipitation of various materials and minerals on metal surfaces to form various types of scales, which can enhance corrosion by trapping materials near the affected surface and/or prevent access for remedial compounds such as corrosion inhibitors. For steel and other commonly used metals, the corrosion rate is sufficient to saturate the Helmholtz layers at the metal surface with ferrous ions and concurrent local pH increases due to the cathodic reduction processes. Combined with the presence of bicarbonates in solution from carbonic acid dissolution, the conditions favor the formation of siderite (ferrous carbonate) scale.

Scales formed on tubing and equipment must be removed to prevent issues with stuck equipment and the progression of corrosion underneath the scale leading to through wall penetrations. One method of countering scaling is the introduction of film-forming corrosion inhibitors that prevent or mitigate corrosion by preventing corrosive substances from reaching the metal surface. However, there are competing reactions of scaling and corrosion inhibitor film formation that begin to favor scale formation as temperature increases. Moreover, solubility issues limit the choices for scale inhibitors that effectively treat metal scaling in brines and other wellbore fluids, with many of the available choices only sequestering iron ions from the surface, which can actually increase the ion availability and corrosion rate in some cases. To compensate for the reduction in efficacy due to temperature, corrosion inhibitors are often added at high dosage rates, which can affect the quality of downstream products.

In one or more embodiments, corrosion inhibitors in accordance with the present disclosure may form films that maintain protective qualities against corrosion and scale formation in high temperature applications such as ≥150° C. Heterocyclic diamine corrosion inhibitors in accordance with the present disclosure may exhibit limited solubility in production fluids, while exhibiting a degree of surface activity that enables the formation of a film of corrosion inhibitor on processing equipment and pipework. The formation of surface films by corrosion inhibitors may be associated with sustained inhibition effects and maintenance of active concentration levels, particularly during the production of hydrocarbon fluids.

Corrosion inhibitors in accordance with the present disclosure may prevent or minimize corrosion by forming a hydrophobic barrier film through physisorption and/or chemisorption, which isolates the metal surface from corrosive media. While not limited to a particular theory, it is believed that the polar heterocyclic head group may be responsible for interacting with the metal surface, anchoring the inhibitor molecule, while a hydrophobic tail is responsible for film formation through hydrophobic interactions with neighboring inhibitor molecules.

Heterocyclic Diamine Corrosion Inhibitor

Corrosion inhibitor compositions in accordance with the present disclosure may include one or more heterocyclic diamines. In one or more embodiments, corrosion inhibitors may include organic compounds may have a general structure that include a polar heterocyclic head group containing electron-rich heteroatoms, and a hydrophobic tail group composed of a saturated or unsaturated hydrocarbon chain.

In one or more embodiments, heterocyclic diamine corrosion inhibitors may have a general structure as shown in Formula (I), where R1 and R2 are independently selected from hydrogen and a C2-C30 saturated or unsaturated hydrocarbon radical, with the proviso that at least one of R1 and R2 is not hydrogen; R3 is hydrogen or a C1-C30 saturated or unsaturated, aromatic or non-aromatic hydrocarbon radical; and n is an integer between 1 and 4.

In one or more embodiments, heterocyclic diamine corrosion inhibitors may be prepared from an annulation reaction by an alkyl diamine component and an aldehyde component. The alkyl diamine component may be of the general formula (II), where n is an integer between 3 and 6, and R4 and R5 are independently H or a C2-C30 saturated or unsaturated hydrocarbon radical such an alkyl, alkylene, alkynyl, and the like.

$$R4NH(CH_2)_nNHR5 \qquad (II)$$

In some embodiments, the alkyl diamine component may be an N-substituted diamine having a straight chain or branched alkyl or alkenyl substituent, including, for example, n-hexyl, n-heptyl, n-octyl, 2-ethylhexyl, n- and iso-nonyl, n- and iso-decyl, n-undecyl, n-dodecyl, n-tetradecyl, n-hexadecyl, n-octadecyl, oleyl, linoleyl, linolenyl, and the like.

The aldehyde component may include one or more aldehydes that include, for example formaldehyde and C1-C30 saturated or unsaturated, aromatic or non-aromatic hydrocarbon radicals such as 2-hydroxynapthaldehyde, 7-phenyl-2,4,6-heptatrienal, crotonaldehyde, 2-hexenal, 2-heptenal, 2-octenal, 2-nonenal, 2-decenal, 2-undecenal, 2-dodecenal, 2,4-hexadienal, 2,4-heptadienal, 2,4-octadienal, 2,4-nonadienal, 2,4-decadienal, 2,4-undecadienal, 2,4-dodecadienal, 2,6-dodecadienal, citral, 1-formyl-[2-(2-methylvinyl)]-2-n-octylethylene, cinnamaldehyde, dicinnamaldehyde, p-hydroxycinnamaldehyde, p-methylcinnamaldehyde, p-ethylcinnamaldehyde, p-methoxycinnamaldehyde, p-dimethylaminocinnamaldehyde, p-diethylaminocinnamaldehyde, p-nitrocinnamaldehyde, o-nitrocinnamaldehyde, o-allyloxycinnamaldehyde, 4-(3-propenal)cinnamaldehyde, p-sodium sulfocinnamaldehyde, p-trimethylammoniumcinnamaldehyde sulfate, p-trimethylammoniumcinnamaldehyde o-methylsulfate, p-thiocyanocinnamaldehyde, p-(S-acetyl)thiocinnamaldehyde, p-(S-N,N-dimethylcarbamoylthio)cinnamaldehyde, p-chlorocinnamaldehyde, 5-phenyl-2,4-pentadienal, 5-(p-methoxyphenyl)-2,4-pentadienal, 2,3-diphenylacrolein, 3,3-diphenylacrolein, α-methylcinnamaldehyde, β-methylcinnamaldehyde, α-chlorocinnamaldehyde, α-bromocinnamaldehyde, α-butylcinnamaldehyde, α-amylcinnamaldehyde, α-hexylcinnamaldehyde, 2-(p-methylbenzylidene)decanal, α-bromo-p-cyanocinnamaldehyde, α-ethyl-p-methylcinnamaldehyde, p-methyl-α-pentylcinnamaldehyde, 3,4-dimethoxy-α-methylcinnamaldehyde, α-[(4-methylphenyl)methylene]benzeneacetaldehyde, α-(hydroxymethylene)-4-methylbenzylacetaldehyde, 4-chloro-α-(hydroxymethylene)benzeneacetaldehyde, α-nonylidenebenzeneacetaldehyde, and the like.

Aldehydes in accordance with the present disclosure may also include heteroaromatic substituted aldehydes such as pyridine-2-carboxaldehyde, pyridine-4-carboxaldehyde, alkylpyridinium aldehyde derivatives, furfuraldehydes, and the like. In one or more embodiments, aldehydes may include aldoses and other reducing sugars of any stereochemistry that include glyceraldehydes, pentoses, hexoses, and the like. In some embodiments, the aldehyde component may be generated from an aldehyde precursor such as paraformaldehyde, acetal, and the like.

While not limited to a particular theory, heterocyclic diamine corrosion inhibitors in accordance with the present disclosure may undergo ring opening reactions at elevated temperatures, releasing carbon monoxide that reacts with metal surfaces and enhance corrosion resistance. In some embodiments, the aldehyde component may be a non-enolizable aldehyde, which generates a stable radical following the ring opening and carbon monoxide forming reaction.

Corrosion inhibitor compositions in accordance with the present disclosure may contain a percent by weight (wt %) of heterocyclic diamine that ranges from a lower limit selected from any of 5 wt %, 10 wt %, and 25 wt %, to an upper limit selected from any of 25 wt %, 50 wt %, and 75 wt %, where any lower limit may be paired with any upper limit.

In one or more embodiments, heterocyclic diamine corrosion inhibitors may be added to a process stream at a dosage of 0.1 ppm to 10,000 ppm by weight, 1 to 1,000 ppm by weight, or 10 to 500 ppm by weight. Furthermore, the corrosion inhibitors as individually disclosed herein may be used alone or in combination with other corrosion inhibitors to enhance a corrosion inhibition performance.

Synergist

In one or more embodiments, corrosion inhibitor compositions may include one or more synergists that increase the corrosion inhibition performance. Synergists in accordance with the present disclosure may include mercaptoethanol, mercaptopropanol, 1-mercapto-2-propanol, 2-mercaptobutanol, and the like; di- or poly-mercapto organic compounds such as di-mercapto derivatives of thiophene, pyrrole, furane, diazoles, and thiadiazoles; di- and tri-mercapto derivatives of pyridine, diazines, triazines benzimidazole, benzthiazole, thioglycolic acid, potassium iodide, and the like.

Corrosion inhibitor compositions in accordance with the present disclosure may contain a percent by weight (wt %) of synergist that ranges from a lower limit selected from any of 0.5 wt %, 1 wt %, and 1.5 wt %, to an upper limit selected from any of 2.5 wt %, 5 wt %, and 7.5 wt %, where any lower limit may be paired with any upper limit.

Base Fluids

Corrosion inhibitor compositions in accordance with the present disclosure may be formulated to contain one or more base fluids. Base fluids may be oleaginous or aqueous and may include emulsions, foams, and other multiphase mixtures. In various embodiments, the aqueous fluid may be a brine, which may include seawater, aqueous solutions wherein the salt concentration is less than that of sea water, or aqueous solutions wherein the salt concentration is greater than that of sea water. Salts that may be found in seawater include, but are not limited to, sodium, calcium, aluminum, magnesium, potassium, strontium, and lithium salts of chlorides, bromides, carbonates, iodides, chlorates, bromates, formates, nitrates, oxides, sulfates, silicates, phosphates and fluorides. Salts that may be incorporated in a brine include any one or more of those present in natural seawater or any other organic or inorganic dissolved salts.

Suitable oleaginous or oil-based fluids that may be used to formulate emulsions may include a natural or synthetic oil and in some embodiments, in some embodiments the oleaginous fluid may be selected from the group including diesel oil, mineral oil, a synthetic oil, such as hydrogenated and unhydrogenated olefins including polyalpha olefins, linear and branch olefins and the like, polydiorganosiloxanes, siloxanes, or organosiloxanes, esters of fatty acids, specifically straight chain, branched and cyclical alkyl ethers of fatty acids, mixtures thereof and similar compounds known to one of skill in the art; and mixtures thereof.

In one or more embodiments, base fluids may include solvents considered as mutual solvents. The use of the term "mutual solvent" includes its ordinary meaning as recognized by those skilled in the art, as having solubility in both aqueous and oleaginous fluids. In some embodiments, the mutual solvent may be substantially completely soluble in aqueous and oleaginous phases, while in other embodiments, a lesser degree of solubilization within a selected phase may be acceptable.

Illustrative examples of such mutual solvents include, alcohols, linear or branched such as isopropanol, methanol, glycerol, or glycols and glycol ethers such as 2-methoxyethanol, 2-propoxyethanol, 2-ethoxyethanol, diethylene glycol monoethyl ether, dipropylene glycol monomethyl ether, tripropylene glycol monomethyl ether, ethylene glycol monobutyl ether, ethylene glycol dibutyl ether, diethylene glycol monoethyl ether, diethyleneglycol monomethyl ether, tripropylene butyl ether, dipropylene glycol butyl ether, diethylene glycol butyl ether, butylcarbitol, dipropylene glycol methyl ether, propylene glycol n-propyl ether, propylene glycol t-butyl ether, ether, and various esters, such as ethyl lactate, propylene carbonate, butylene carbonate, and the like, and pyrrolidones.

Base fluids in accordance with the present disclosure may be a percent by volume (vol %) of a corrosion inhibitor composition in a range of 2.5 vol % to 30 vol % in some embodiments, and from 5 vol % to 25 vol % in other embodiments.

Example 1: Corrosion Inhibition Performance of Diamines

In this example, a series of diamines were assayed for corrosion inhibition performance by observing corrosion on steel coupons placed in a brine solution with a selected corrosion inhibitor. Acyclic diamine Duomeen T was assayed alongside various heterocyclic diamines. Heterocyclic diamines in accordance with the present disclosure were prepared from a reaction of a diamine and formaldehyde to generate hexahydropyrimidine with a pendant alkyl chain having the general structure (I) discussed above. E1 is a diamine in which R1 is a mixture of alkyl chains derived a tallow fatty acid complex containing 26% palmitic acid, 14% stearic acid, 3% myristic, 47% oleic acid, 3% linoleic, and 1% linolenic; and R2 and R3 are hydrogen. For E2-E6, pendant chains R1 were derived from tallow fatty acid, while R2 is independently various lengths of oligomerized ethylene oxide (6-14 repeats), and R3 is hydrogen for all samples.

Corrosion inhibitor samples were then dispersed in a brine medium and steel coupons were submerged therein. The samples were then placed in an autoclave at 150° C. for 48 hours. The conditions for autoclave testing of samples are summarized below in Table 1.

TABLE 1

| Test conditions for Example 1 | |
|---|---|
| Temperature | 150° C. |
| pp $CO_2$ | 1 barg |
| Brine | 3% NaCl |
| Water Cut | 100% |

TABLE 1-continued

Test conditions for Example 1

| | |
|---|---|
| Duration | 48 hrs |
| Concentration of Corrosion Inhibitor Formulation* | 500 ppm |
| Concentration of Active | 100 ppm |

*containing 20 wt % active inhibitor and 1 wt % mercaptoethanol

Results are plotted in the bar chart depicted in FIG. 1. The results indicate that samples E2-E6, containing oligomers of ethylene oxide, exhibited higher rates of corrosion compared to acyclic diamine Duomeen T and heterocyclic diamine E1. Corrosion was also characterized by the formation of a dark siderite scale.

Example 2: Corrosion Characterization

In the next example, metal coupons were treated with Duomeen T and the heterocyclic diamine E1 substantially as discussed above in Example 1, but with the introduction of an added oil phase to simulate field conditions. Similar to the results in Example 1, siderite scale was formed on the metal coupons. Samples were formulated as shown in Table 2, where the balance of the inhibitor composition was ethylene glycol monobutyl ether (EGMBE).

To characterize the durability of the developed scale, sample coupons were treated to remove siderite scale that accumulated during testing. Following aging, samples were removed from the autoclave and treated with Clark's solution, a mixture of hydrochloric acid and di-n-butyl thiourea, to remove surface scaling. Samples were soaked in Clark's solution for 75 minutes to remove siderite scale. The results are given in Table 2.

TABLE 2

Performance of acyclic and heterocyclic diamines in 80:20 partitioned autoclaves

| Inhibitor Formulation | Concentration (ppm) | Corrosion Rate (MPY) |
|---|---|---|
| 20% E1 and 1% mercaptoethanol | 500 | 6.82 |
| 20% E1 and 1% mercaptoethanol | 500 | 6.44 |
| 20% Duomeen T and 1% mercaptoethanol | 500 | −5.74* |
| 20% Duomeen T and 1% mercaptoethanol | 500 | −5.74* |

In all cases, the comparative acyclic amine Duomeen T exhibited a tendency to form a tightly adhered siderite scale on their surfaces that was extremely difficult to remove. Heterocyclic diamine samples exhibited some siderite scale, but the scale was considerably less dense and easier to remove from the metal surface when compared to the acyclic samples.

The negative corrosion rates (denoted with*) with Duomeen T are due to the buildup of siderite corrosion products on the test specimen surfaces, which could not be removed post-processing, resulting in a net weight gain. The performance of heterocyclic diamine E1 under similar conditions gives corrosion rates <8 MPY with siderite that could be removed by processing with Clark's solution.

Example 3: Corrosion Inhibitor Performance in Multiphase Systems

In the next example, further testing was performed to confirm the performance of heterocyclic diamine E1 in a bi-phasic system of 3% sodium chloride brines and an oil phase under substantially the same conditions in Example 1 as applied to coupons prepared from C1018 carbon steel. The results are shown in Table 3.

TABLE 3

Performance of acyclic and heterocyclic diamines in 80:20 partitioned autoclaves

| Inhibitor Formulation | Concentration (ppm) | Corrosion Rate (MPY) | Autoclave |
|---|---|---|---|
| 20% E1 and 1% mercaptoethanol | 500 | 16.12 | 71884 |
| 20% E1 and 1% mercaptoethanol | 500 | 13.68 | 71884 |
| 20% E1 and 1% mercaptoethanol | 500 | 6.17 | 71885 |
| 20% E1 and 1% mercaptoethanol | 500 | 6.75 | 71885 |
| 20% E1 and 1% mercaptoethanol | 500 | 5.95 | 71886 |
| 20% E1 and 1% mercaptoethanol | 500 | 3.59 | 71886 |

Example 4: Effect of Brine Strength

In the next example, the effect of the brine salinity (total dissolved solids, TDS) on the high temperature performance of heterocyclic diamine in various concentration so sodium chloride brine (10, 15, 25% NaCl). Testing conditions were substantially the same as those in Example 1 and the results are shown in Table 4.

TABLE 4

Performance of heterocyclic diamine E1 in various brine concentrations

| Inhibitor Formulation | Concentration (ppm) | Salinity (%) | Corrosion Rate (MPY) |
|---|---|---|---|
| 20% E1 and 1% mercaptoethanol | 500 | 10 | 5.47 |
| 20% E1 and 1% mercaptoethanol | 500 | 10 | 6.72 |
| 20% E1 and 1% mercaptoethanol | 500 | 15 | 5.26 |
| 20% E1 and 1% mercaptoethanol | 500 | 15 | 3.41 |
| 20% E1 and 1% mercaptoethanol | 500 | 25 | 8.74 |
| 20% E1 and 1% mercaptoethanol | 500 | 25 | 8.70 |

It therefore appears that heterocylic diamine E1 functions well over wide ranging brine salinities with arguably a slight drop in performance at the higher TDS conditions.

Example 5: Elevated Temperature Performance

E1 has shown continued performance at 150° C. over a range of brine salinities. Testing was performed under essentially the same conditions as Example 1, but the test temperature was increased to 175° C. in a bi-phasic system at two different dose rates of 500 ppm and 1000 ppm. Given that siderite scale often exhibits a decreased solubility with increasing temperatures, exposure to Clark's solution was recorded at two time points, 30 and 60 minutes. Results are shown in Table 5.

TABLE 5

Performance of heterocyclic diamine E1 at 175° C.

| Inhibitor | Clark's exposure (min) | Dose (ppm) | Corrosion Rate (MPY) |
|---|---|---|---|
| 20% E1 and 1% mercaptoethanol | 30 | 500 | 3.13 |
| 20% E1 and 1% mercaptoethanol | 30 | 500 | 1.14 |
| 20% E1 and 1% mercaptoethanol | 30 | 1000 | 5.33 |
| 20% E1 and 1% mercaptoethanol | 30 | 1000 | 7.34 |
| 20% E1 and 1% mercaptoethanol | 60 | 500 | 12.46 |
| 20% E1 and 1% mercaptoethanol | 60 | 500 | 9.99 |
| 20% E1 and 1% mercaptoethanol | 60 | 1000 | 12.91 |
| 20% E1 and 1% mercaptoethanol | 60 | 1000 | 11.56 |

With a 30 minute exposure in Clark's solution, it appears from the corrosion rate data that 500 ppm E1 appears better than 1000 ppm, however this is related to scale formation on the surface. After a 60 minute exposure to Clark's the corrosion rates of the 500 ppm and 1000 ppm tests converge and are very similar in magnitude at about 11-12 MPY.

Application

Heterocyclic diamine corrosion inhibitors in accordance with the present disclosure effectively prevent and/or inhibit the formation of corrosion on metal materials and equipment, such as metal piping and flow lines that are used in various wellbore operations. Corrosion inhibitors in accordance with the present disclosure may be applied to metal surfaces by injection downhole, spraying, dipping and the like.

In one or more embodiments, corrosion inhibitors may be added to a process stream that contacts a metal surface, covering and maintaining an effective application on the surface. Process streams may include a number of components, including water, petroleum, petroleum products, hydrocarbons, and acidic species such as $CO_2$ and $H_2S$, and salts such as NaCl. Introduction of a corrosion inhibitor to a process stream may include injection of the corrosion inhibitor composition into a process stream at various intervals along a pipeline, well, or other conduit.

Although only a few examples have been described in detail above, those skilled in the art will readily appreciate that many modifications are possible in the examples without materially departing from this subject disclosure. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112 (f) for any limitations of any of the claims herein, except for those in which the claim expressly uses the words 'means for' together with an associated function.

What is claimed:

1. A composition, comprising:
a corrosion inhibitor comprising a synergist comprising mercaptoethanol and a heterocyclic diamine corrosion inhibitor represented by the formula:

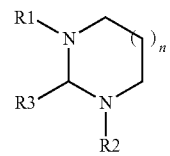

wherein R1 and R2 are independently selected from hydrogen and a C2-C30 saturated or unsaturated hydrocarbon radical, with the proviso that at least one of R1 and R2 is not hydrogen; R3 is hydrogen or a C1-C30 saturated or unsaturated, aromatic or non-aromatic hydrocarbon radical; and n is 1.

2. The composition of claim 1, wherein the C2-C30 saturated or unsaturated hydrocarbon radical comprises an acid selected from the group consisting of palmitic acid, stearic acid, myristic acid, oleic acid, linoleic acid, and linolenic acid.

3. The composition of claim 1, wherein R3 is a C1-C30 saturated or unsaturated, aromatic or non-aromatic hydrocarbon radical.

4. The composition of claim 1, wherein R3 is hydrogen.

5. The composition of claim 4, wherein R1 is a C2-C30 saturated or unsaturated hydrocarbon radical and R2 is hydrogen.

6. The composition of claim 4, wherein R2 is a C2-C30 saturated or unsaturated hydrocarbon radical and R1 is hydrogen.

7. The composition of claim 1, further comprising a mutual solvent that is soluble in both aqueous and oleaginous fluids.

8. The composition of claim 7, wherein the mutual solvent comprises one or more solvents selected from the group consisting of isopropanol, methanol, glycerol, 2-methoxyethanol, 2-propoxyethanol, 2-ethoxyethanol, diethylene glycol monoethyl ether, dipropylene glycol monomethyl ether, tripropylene glycol monomethyl ether, ethylene glycol monobutyl ether, ethylene glycol dibutyl ether, diethyleneglycol monomethyl ether, tripropylene butyl ether, dipropylene glycol butyl ether, diethylene glycol butyl ether, butylcarbitol, dipropylene glycol methyl ether, propylene glycol n-propyl ether, propylene glycol t-butyl ether, ethyl lactate, propylene carbonate, butylene carbonate, and pyrrolidone.

9. The composition of claim 8, wherein the mutual solvent comprises ethylene glycol monobutyl ether.

10. The composition of claim 1, wherein the mercaptoethanol is present in the range of 1 wt % to 5 wt %.

11. A method, comprising:
contacting a metal surface with a corrosion inhibitor composition, wherein the corrosion inhibitor composition comprises a synergist comprising mercaptoethanol and a heterocyclic diamine corrosion inhibitor represented by the formula:

wherein R1 and R2 are independently selected from hydrogen and a C2-C30 saturated or unsaturated hydrocarbon radical, with the proviso that at least one of R1 and R2 is not hydrogen; R3 is hydrogen or a C1-C30 saturated or unsaturated, aromatic or non-aromatic hydrocarbon radical; and n is 1.

12. The method of claim 11, wherein the metal surface comprises a wellbore tool or a pipe disposed in a wellbore.

13. The method of claim 12, wherein contacting the metal surface comprises spraying the metal surface with the corrosion inhibitor composition, dipping the metal surface into the corrosion inhibitor composition, or adding the corrosion inhibitor composition to a process stream comprising at least one of water, petroleum, or petroleum products.

14. The method of claim 13, further comprising contacting the metal surface with the process stream.

15. The method of claim 14, further comprising adding the corrosion inhibitor composition to a conduit or a wellbore containing the process stream.

16. The method of claim 15, wherein adding the corrosion inhibitor composition is continuous or intermittent.

17. The method of claim 11, wherein:
R1 is a C2-C30 saturated or unsaturated hydrocarbon radical;
R2 is hydrogen;
R3 is hydrogen; and
n is 1.

18. The method of claim 11, wherein the mercaptoethanol is in the range of 1 wt % to 5 wt %.

19. The method of claim 11, wherein the corrosion inhibitor composition further comprises a mutual solvent.

* * * * *